United States Patent [19]

Blumenthal et al.

[11] 4,101,404
[45] Jul. 18, 1978

[54] HOT GAS MEASURING DEVICE

[76] Inventors: Robert N. Blumenthal, 17470 Bard Ct., Brookfield, Wis. 53005; Andreas T. Melville, 204 N. 86th St., Wauwatosa, Wis. 53226

[21] Appl. No.: 700,659

[22] Filed: Jun. 28, 1976

[51] Int. Cl.² ............................................. G01N 27/46
[52] U.S. Cl. ................................................. 204/195 S
[58] Field of Search ............... 204/1 S, 195 S; 324/29

[56] References Cited

U.S. PATENT DOCUMENTS 3,960,692  6/1976  Weyl et al. ...................... 204/195 S

FOREIGN PATENT DOCUMENTS 2,401,134  8/1974  Fed. Rep. of Germany ... 204/195 S

Primary Examiner—G. L. Kaplan
Attorney, Agent, or Firm—Wheeler, Morsell, House & Fuller

[57] ABSTRACT

A probe comprising a tube made of solid electrolyte material is slidably mounted within a ceramic support tube which is mounted to project into the interior of a furnace. The end of the electrolyte tube is closed and the support tube has open ports or windows therein which expose the exterior end surface of the electrolyte tube to the hot furnace gases and causes a voltage to develop between the interior and the exterior surfaces of the electrolyte tube which is indicative of a furnace gas characteristic. A first electrode is supported between the ends of the electrolyte tube and the support tube, and a second electrode is supported within the inner end of the electrolyte tube. A hollow cylindrical cap is adjustably mounted adjacent the outer end of the electrolyte tube and contains an internal spring which urges the closed end of the electrolyte tube against the first electrode to maintain good electrical contact therebetween in spite of corrosive reaction of the electrode with the hot furnace gases or the electrolyte. To prolong the life of the electrode, it is preferably made either of two noble metal wire screens mounted in face-to-face relationship, or it is made of a chemically stable electronic ceramic conductor such as cation-doped lanthanum chromite, which is substantially inert with respect to known electrolytes and known hot furnace gases.

11 Claims, 4 Drawing Figures

HOT GAS MEASURING DEVICE

BACKGROUND OF THE INVENTION

This invention relates to the measurement of gas characteristics through the use of a probe comprising a solid electrolyte which is in contact on one side or face with a reference gas such as the ambient atmosphere and is in contact on the opposing side or face with a hot gas whose characteristics are to be measured. In such a probe, a voltage is generated between the two sides or faces of the solid electrolyte, the magnitude of the voltage being dependent upon the temperature of the electrolyte and on the ratio of the oxygen partial pressure on opposing sides or faces of the electrolyte. This principle has been used in the past to measure the oxygen partial pressure of hot furnace gases with various different oxygen sensors, such as disclosed in U.S. Pat. Nos. 3,454,486; 3,546,086 and 3,596,345 and British Pat. No. 1,296,995.

Although the principle of operation of the above-noted type of oxygen sensors is quite simple, the utilization of such oxygen sensors in industrial applications has been limited in the past due to several practical problems. First, the solid electrolyte, which is a ceramic material, is hard and brittle and is thus very susceptible to thermal shock and/or mechanical damage. Another problem has been the detachment of the electrode from the surface of the electrolyte due to corrosion of the electrodes. The latter problem occurs even when the electrodes are made of a noble metal, such as platinum. For example, platinum reacts at high temperatures and low oxygen pressures with stabilized zirconia electrolyte material, which is commonly used in this type of oxygen sensor to form $ZrPt_3$. The reaction product is in the form of fragments or dust which drops away from the electrode, thus reducing the thickness thereof and eventually breaking the electrical contact between the electrode and the electrolyte or loosening the electrode sufficiently in its mounting to allow it to be blown away by the gas stream under measurement. For the above reasons, the useful working life of the above-noted type of oxygen sensor has been limited in the past and has limited their potential range of application.

SUMMARY OF THE INVENTION

The principal object of this invention is to provide a novel gas measuring device which has a longer working life than those heretofore known. In accordance with this invention, the problem of electrode corrosion is solved in one embodiment of the invention by using multiple layers of a noble metal mesh screen as the outer electrode which is exposed to the hot gases under measurement. This arrangement increases the over-all thickness of the electrode so that as the wires disintegrate and flake off, there will be ample reserve electrode wire remaining to function as a conductor. Even though there are several layers, the mesh form of the wires provides for flow of gas through the electrode. The undulating configuration of the wires in the mesh provides many points of contact between one mesh and the next, and with the electrolyte. The electrode is spring loaded to continually press one mesh screen against the other, and with the electrolyte, thus to take up any void space as the electrode wire disintegrates and fragments thereof drop off or are blown off.

In another embodiment of the invention, the electrode comprises a chemically stable electronic ceramic conductor which is relatively inert with respect to known hot furnace gases and known solid electrolytes and to the electric lead wires coupled thereto. Accordingly, it resists corrosion and disintegration.

Both of the above-mentioned electrode embodiments substantially extend the working life of the electrode and enable the oxygen sensor to be applied to industrial applications which were heretofore impractical because of the relatively short working life of prior art electrodes.

Another feature of the invention is compressively loading the electrolyte and electrode with a novel spring mounting which includes a hollow cap adjustably mounted on the outer end of the electrolyte tube and an internal spring within the cap urging the electrolyte tube inwardly against the electrode. The above-noted prior U.S. Pat. No. 3,454,486 discloses the use of a leaf spring for compressively loading the inner electrode of an oxygen sensor against the inner surface of the electrolyte tube thereof. However, this leaf spring arrangement is not adjustable and acts on the inner electrode rather than the outer electrode, which is subject to the most severe corrosion due to its exposure to the hot furnace gases. Instead of compressively loading the outer electrode against a ceramic supporting tube, as is the case of the instant invention, the above-noted U.S. Pat. No. 3,454,486 specifies that the outer electrode be cemented to the outside surface of the electrolyte tube by means of a refractory cement.

The preferred spring adjustment features locates the spring interiorly of the hollow cap and the cap is provided with a viewing port or window so the operator can view the spring and perceive its state of compression.

Other objects, features and advantages of the invention will appear from the disclosure hereof.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Figure 1:
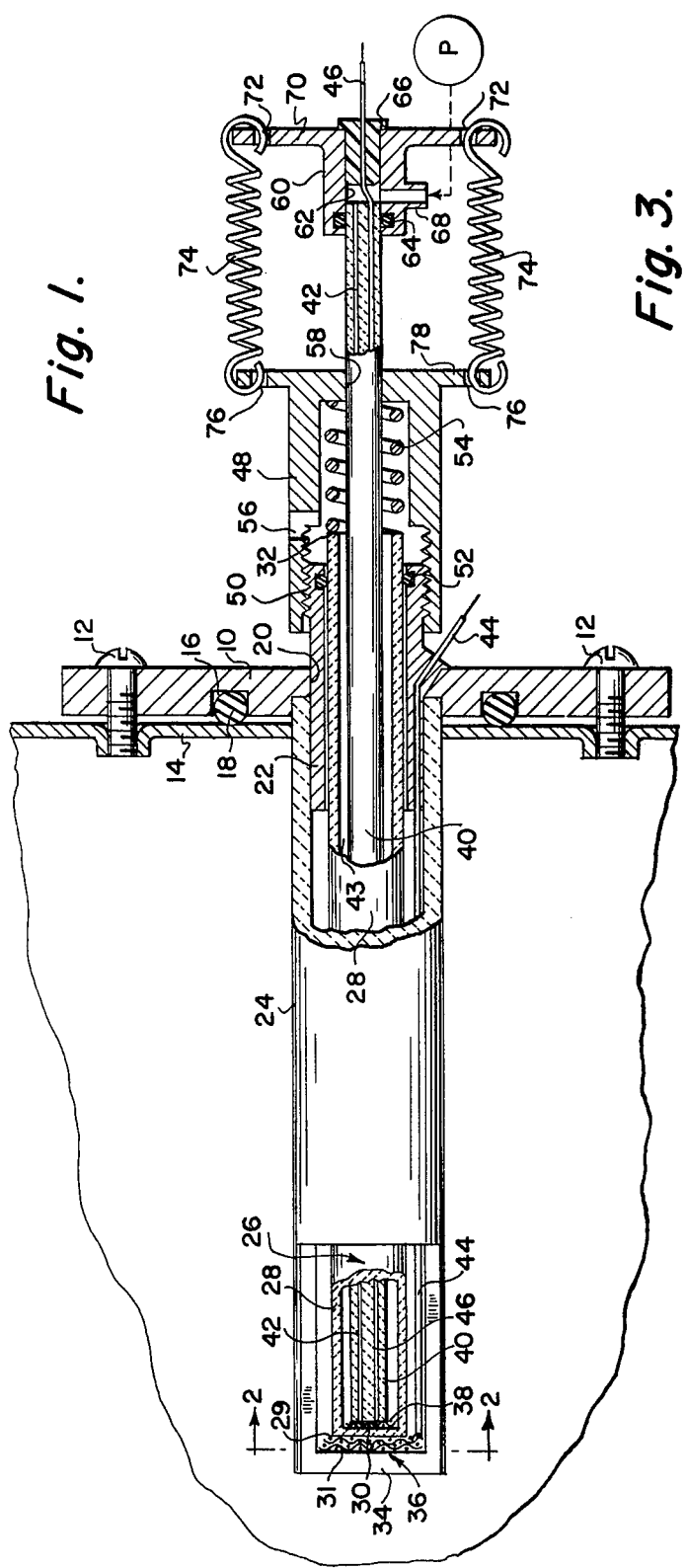
FIG. 1 is a side view of one embodiment of the probe mounted to extend within a furnace, various portions of the probe being partially cut away and shown in longitudinal section to reveal inner details.

Referring to FIG. 1, the mounting structure for this embodiment includes a circular metal flange 10 which has holes formed in the periphery thereof to receive bolts 12 for fastening flange 10 to a port 14 on the side wall of a furnace. A circular groove 16 is formed in the inner surface of flange 10 for receiving an O-ring 18 which acts as a gas seal. Welded in the center of flange 10 is a metal sleeve 22 which supports a ceramic support tube 24 that extends into the interior of the furnace.

Support tube 24 has cut away portions which form open ports or windows 26 on opposing sides of tube 24 near its end. A smaller tube 28 which is made of a solid electrolyte material and has a closed end 30 adjacent ports 26 of tube 24 inside the furnace and an open end 32 outside the furnace is slidably mounted within metal sleeve 22 and extends through support tube 24 and terminates near the bottom end 34 thereof.

Electrolyte tube 28 is preferably made of calcia stabilized zirconia although other electrolytes could be used such as $Y_2O_3$ stabilized zirconia, calcia-doped thoria, etc. However, the calcia-stabilized zirconia is preferable because it is believed to possess better thermal shock characteristics than the other common solid electrolyte materials. The ceramic material used for support tube 24 is preferably alumina, which has good thermal shock characteristics and also has a coefficient of thermal expansion which closely matches that of the calcia-stabilized zirconia.

A first electrode 36 is mounted between the outer face of the inner end 30 of electrolyte tube 38 and the inner face of the end wall 34 of support tube 24. A second electrode 38 is mounted on the opposite side of the end wall 30 of electrolyte tube 28 between the inner face of said end wall 30 and the end of a ceramic rod 40 mounted within electrolyte tube 28. Ceramic rod 40 is preferably made of alumina and has one or more longitudinal bores 42 through which a reference gas such as the ambient atmosphere is admitted to the interior face of electrolyte end wall 30 while the exterior face thereof is in contact with the hot furnace gases admitted through ports or windows 26. The reference gas is fed to bore 42 through side port 68 (FIG. 1) and is exhausted through the space 43 about the tube 28 and through its open end 32. As noted above, when the interior surface of electrolyte tube 28 is exposed to a reference gas and the exterior thereof is exposed to the hot gases which are to be measured, a voltage is generated between the exterior and interior surfaces of the electrolyte tube end wall 30. The magnitude of the voltage is dependent upon the temperature of the electrolyte material and the oxygen partial pressure ratio between the opposing sides of the electrolyte. Electrodes 36 and 38 serve the function of picking up this voltage difference and conducting it via suitable ceramic insulated conductors 44 and 46 to a suitable conventional measuring instrument (not shown) located at the exterior of the device.

The structure of the first electrode 36 is particularly important in this invention because it is exposed to the hot furnace gases and also is pressed against the end wall 30 of the electrolyte tube 28. Electrode 36 is subject to be corroded either by reaction with some component of the furnace gases or by reaction with the end 30 of the electrolyte tube 28. In accordance with one aspect of this invention, the problem of loss of electrical contact due to such corrosion is obviated by providing an improved electrode structure which either resists such corrosion, or which renews itself as it corrodes, thus to negate the deleterious effects of such corrosion. Such an electrode is subject to the load of an improved bias spring assembly which urges the end wall 30 of electrolyte tube 28 against the electrode 36, thus to maintain good contact therebetween in spite of such corrosion.

Figure 2:
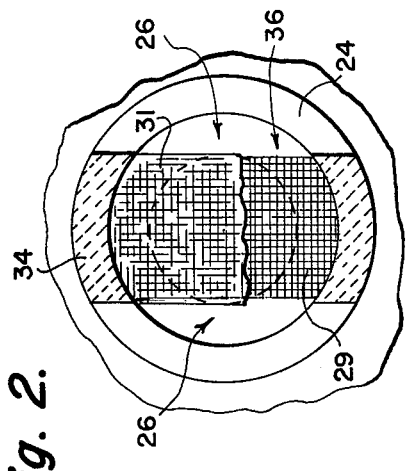
FIG. 2 is a cross sectional view taken on the line 2—2 of FIG. 1.

One embodiment of electrode is shown in FIGS. 1 and 2. It consists of two or more platinum wire screens 29, 31 which are welded or otherwise held together in face-to-face contact or assembly 36 with each other. The planes of the assembled screens 29, 31 are transverse to the axis of electrolyte tube 28. The undulations of the wires in screens 29, 31 provide good point contact of one screen with the other and with the electrolyte. By having more than one screen layer, there will be ample reserve of electrode wire which will continue to function even as the wire corrodes or disintegrates and fragments thereof flake or dust off. The spring loading on electrolyte tube 28 causes electrolyte tube 28 to advance toward electrode 36 as the contact portions of the platinum in the electrode 36 react with the zirconia in the electrolyte tube 28 to cause disintegration of the electrode and gradual reduction of electrode thickness and thus maintains good electrical contact with the platinum screen electrode assembly 36 even though corrosion does occur. The reaction product which is formed between the platinum wire electrode and the end of the electrolyte tube 28 is typically in the form of a dust which falls downwardly from the screen and exposes fresh platinum for electrical contact purposes. Mesh screens 29, 31 can be fabricated of noble metal or noble metal alloy wires other than platinum, for example, the platinum-rhodium alloy wires, gold wires and gold-palladium alloy wires referred to in British Pat. No. 1,296,995.

Electrode 38 is also desirably a noble metal mesh screen, but it need only comprise a single layer screen rather than a multiple layer screen because the relatively high oxygen pressure in the atmosphere which contacts the electrode 38 inhibits the corrosive reaction thereof against the electrolyte tube 28 and screen 38 is not exposed to the hot gases in the furnace. Accordingly, screen 38 is not as subject to corrosion and disintegration as is electrode 36.

The compressive load is maintained between electrolyte tube 28 and electrode 36 by means of an improved spring mounting assembly which includes a hollow cylindrical cap 48 which is threaded to the outer end of sleeve 22 by screw threads 50. The hot gases which are admitted to the interior of support tube 24 are prevented from entering cap 48 by means of an O-ring seal 52 between electrolyte tube 28 and sleeve 22. A compression spring 54 is mounted interiorly within cap 48 and bears against the outer end 32 of electrolyte tube 28 and thus urges electrolyte tube 28 against electrode 36. The amount of pressure of spring 54 can conveniently be adjusted by simply turning cap 48. A viewing port 56 is formed in the central portion of cap 48. By observing the position of spring 54 through port 56 as cap 48 is being turned, the operator can perceive an approximate indication of the amount of change of spring pressure for a given amount of turning, and the compression of the spring. If desired, a more accurate scale could be marked on the cap 48 and the adjacent portion of sleeve 22.

Cap 48 has a central opening 58 in its outer end through which ceramic rod 40 slidably extends. A cap 60 is mounted by O-ring 64 on the outer end of rod 40. Cap 60 has a central bore 62 which is sealed against rod 40 on its inner end by an O-ring 64 and is plugged on its outer end by a flexible insulating plug 66 through which electrical conductor 46 extends. A gas inlet port 68 extends from the side wall of sleeve 60 and communicates into bore 62 for introducing a reference gas such as the ambient atmosphere into the interior of electrolyte tube 28 via one or more of the longitudinal bores 42 in rod 40. The reference gas which is thus introduced into the interior of electrolyte tube 28 escapes through the open end 32 thereof and the opening 56 in cap 48.

Sleeve 60 has a circular flange 70 on its outer end which has two openings 72 formed on opposing sides thereof for receiving the ends of springs 74 which are secured at their other ends to openings 76 in a flange 78 on the outer end of end cap 48. Springs 74 urge rod 40 inwardly against electrode 38, thus to maintain good contact between electrode 38 and the closed end 30 of electrolyte tube 28. It should be noted that when the end cap 48 is rotated to change the tension of spring 54, the tension is also changed on the springs 74 in the same direction, i.e., when cap 48 is turned in a direction to increase the pressure on first electrode 36, the pressure on second electrode 38 is also increased, and vice versa.

Figure 3:
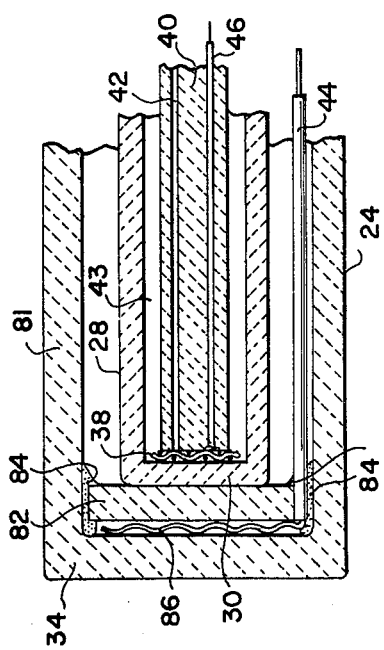
FIG. 3 is a fragmentary enlarged longitudinal sectional view of a modified embodiment of the invention in which the electrode comprises an electronic ceramic disk.
Figure 4:
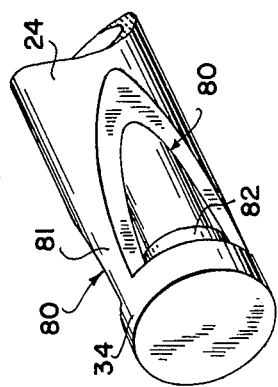
FIG. 4 is a fragmentary perspective view of the end of the probe of the FIG. 3 embodiment.

FIGS. 3 and 4 show a modification in which the electrode between the electrolyte 28 and the end wall 34 of tube 24 comprises an electronic ceramic conductor. In this modification, open windows or ports 80 are cut in opposite sides of tube 24 to expose portions of the side edges of a disk-shaped electronic ceramic electrode 82. End wall 34 of tube 24 remains connected to the main body of tube 24 by bridges 81. Electrode disk 82 is cemented by refractory cement 84 into the closed end 34 of support tube 24 over the top of a wavy platinum wire 86 which is connected to the end of conductor 44, which serves to make contact with the outer face of electrode disk 82. The refractory cement 84 completely seals around the entire periphery of the electrode disk 82 so as to isolate and seal the platinum wire 86 from contact with the hot furnace gases. However, the hot furnace gases do contact the inner surface of electrode disk 82 and the outer surface of the end wall 30 of electrolyte tube 28, thus to generate a voltage difference between electrodes 38 and 82.

The electronic ceramic electrode is compounded of a suitable electronic ceramic conductor means which meets the following requirements:

(a) high electronic conductivity,
(b) chemical and thermodynamic stability,
(c) it should be relatively inert to the electrolyte, the hot furnace gas and the electric lead wire 86 (typically platinum) which is coupled thereto.

Electronic ceramic conductor means meeting these requirements are discussed in detail in the scientific literature, for example, in the book entitled "Electrical Conductivity in Ceramics and Glass" published by Marcel Dekker, Inc. in 1974, Parts A and B, Edited by N. M. Tallan, see particularly Chapter 6—Highly-Conducting Ceramics and the Conductor-Insulator Transition, and the article of D. B. Meadowcroft in the British Journal of Applied Physics of 1969, Ser. 2, Vol. 2, page 1,225 et seq. entitled "Some properties of strontium-doped lanthanum chromite".

Of the various electronic ceramic conductors which are suited for use in electrode 82, we prefer cation-doped lanthanum chromite compounded by the formula $La_{(1-x)}M_xCrO_3$ where M can be any cation having a valence of $+2$ such as calcium or strontium, or the like. The operative range of values for $x$ is between 0 and 0.25. The above-noted compound solves the problem of electrode corrosion because it is substantially inert to known furnace gases, known solid electrolytes and the noble metal contact wire 86, it has good electrical conductivity and is chemically and thermodynamically stable.

Within the operative range of values for $x$ given above, the preferred range is between 0.15 and 0.25.

Referring again to FIG. 1, the reference gas is pumped by a conventional pump P into port 68 and flows down the bores 42 in rod 40 to the inner end 30 of electrolyte tube 28 and then flows back in the space between the inner surface of tube 28 and the outer surface of rod 40 and is discharged into the atmosphere through opening 56 in cap 48. This is an important feature of the invention because in some instances small cracks will form in electrolyte tube 28 and will admit the furnace gases to the interior of tube 28. Such leaked gases mix with and contaminate the reference gas and produce inaccurate output signals. However, with the above-described routing of the reference gas stream, the leaked gases are flushed by the reference gas stream away from the end 30 of electrolyte tube 28 where the potential difference is measured. Therefore, the reference gas adjacent to end 30 of electrolyte tube 28 is uncontaminated and produces accurate output signals even when there is leakage of gas through other portions of tube 28.

What is claimed is:

1. A gas measuring device for measuring a characteristic of high temperature gases in a furnace having a wall with a port and comprising an axially elongated electrolyte tube having at one end an inside surface and an outside surface, said tube comprising a solid electrolyte material, mounting means for so mounting said tube that one of said surfaces at said one end is adapted to be exposed to a gas whose characteristic is to be measured and the other said surface is adapted to be exposed to a known reference gas, a first electrode, said first electrode being renewable to overcome corrosion, said first electrode comprising multiple layers of an open mesh screen of noble metal, means for holding said first electrode in contact with said outside surface of said end of said electrolyte tube, a second electrode, means for holding said second electrode in contact with said other surface, electrical conductors coupled to said electrodes, said mounting means including a bracket for fastening the device to the furnace wall and including an axially projecting sleeve concentric with the tube and attached to the bracket to provide support for said tube remote from said one end of said electrolyte tube for guiding said electrolyte tube for axial sliding movement within said sleeve and to afford axial shifting of said tube to maintain said tube in contact with said first electrode, and means for biasing said one surface of said one end of said electrolyte tube against said first electrode and comprising a hollow cap attached to said sleeve and a spring within said hollow cap bearing against the outer end of said electrolyte tube to press said one surface of said electrolyte tube against said first electrode to maintain good electrical contact therebetween.

2. The measuring device of claim 1 and further comprising means on said cap for adjusting the pressure of said spring.

3. The measuring device of claim 1 in which said electrolyte tube has a closed end, the opposed faces of which constitute said surfaces, said mounting means comprising a support tube extending beyond the closed end of the electrolyte tube, and having an end wall spaced from the closed end of the electrolyte tube, ports in said support tube to admit said hot gas into contact with said one surface, said first electrode being disposed in the space between the end wall of the support tube and the closed end of the electrolyte tube and subject to the pressure of said spring.

4. The measuring device of claim 1 in which said hollow cap has an opening, said means for holding said second electrode in contact with said other surface comprising a rod extending through said opening and into the interior of the electrolyte tube, the inner end of said rod being adjacent to said other surface, said second electrode being disposed between said rod and said other surface, and spring means urging said rod inwardly toward said other surface to maintain good electrical contact between said second electrode and said other surface.

5. The measuring device of claim 4 and further comprising at least one longitudinal bore in said rod and means for applying a known reference gas to the outer end of said bore for transmission to the said surface of said electrolyte tube at the inner end of said rod.

6. The gas measuring device of claim 5 wherein there is a space between the outer surface of said rod and the inner surface of said electrolyte tube, and further comprising means for pumping said reference gas into the outer end of said bore, said space permitting said reference gas to flow from the inner end of said rod back toward the outer end of the electrolyte tube, thereby flushing any gases that may leak through cracks in the electrolyte tube away from the portion thereof that lies between said first and second electrodes, thus providing accurate output signals in spite of gas leakage through said electrolyte tube.

7. A gas measuring device for measuring a characteristic of high temperature gases comprising an electrolyte tube having an inside surface and an outside surface, said tube comprising a solid electrolyte material, mounting means for so mounting said tube that one of said surfaces is adapted to be exposed to a gas whose characteristic is to be measured and the other said surface is adapted to be exposed to a known reference gas, a first electrode, means for holding said first electrode in contact with said one surface, a second electrode, means for holding said second electrode in contact with said other surface, electrical conductors coupled to said electrodes, said mounting means including a protective sleeve within which said electrolyte tube is slidable, and means for biasing said one surface againt said first electrode and comprising a hollow cap attached to said sleeve and a spring within said hollow cap bearing against the outer end of said electrolyte tube to press said one surface of said electrolyte tube against said first electrode to maintain good electrical contact therebetween, said first electrode comprising multiple layers of an open mesh screen of noble metal.

8. A gas measuring device for measuring a characteristic of high temperature gases comprising an electrolyte tube having an inside surface and an outside surface, said tube comprising a solid electrolyte material, mounting means for so mounting said tube that one of said surfaces is adapted to be exposed to a gas whose characteristics is to be measured and the other said surface is adapted to be exposed to a known reference gas, a first electrode, means for holding said first electrode in contact with said one surface, a second electrode, means for holding said second electrode in contact with said other surface, electrical conductors coupled to said electrodes, said mounting means including a projecting sleeve within which said electrolyte tube is slidable, and means for biasing said one surface against said first electrode and comprising a hollow cap attached to said sleeve and a spring within said hollow cap bearing against the outer end of said electrolyte tube to press said one surface of said electrolyte tube against said first electrode to maintain good electrical contact therebetween, said hollow cap having an opening, said means for holding said second electrode in contact with said other surface comprising a rod extending through said opening and into the interior of the electrolyte tube, the inner end of said rod being adjacent to said other surface, said second electrode being disposed between said rod and said other surface, and spring means urging said rod inwardly toward said other surface to maintain good electrical contact between said second electrode and said other surface, in further combination with a second cap attached to the outer end of said rod, said spring means urging said rod inwardly comprising external springs connected at corresponding ends to the first mentioned cap and connected at corresponding opposite ends to the second cap.

9. The measuring device of claim 8 further comprising at least one longitudinal gas bore in said rod, a gas bore in said second cap communicating with said bore in said rod and a gas inlet port on said second cap communicating with the gas bore therein.

10. In a gas measuring device for measuring a characteristic of high temperature gases, and having a solid electrolyte and means for mounting said electrolyte with a portion of its surface exposed to the gas which is to be measured, and having an electrode in contact with said exposed electrolyte surface and spring means pressing said electrode and electrolyte together, the improvement wherein said electrode comprises at least two open mesh screens made of electrically conductive material, said screens being mounted in face-to-face contact with each other transverse to the direction of action of said spring means.

11. The measuring device of claim 10 in which said screens comprise wire made of noble metal or noble metal alloys.

* * * * *

UNITED STATES PATENT AND TRADEMARK OFFICE
CERTIFICATE OF CORRECTION

PATENT NO. : 4,101,404
DATED : July 18, 1978
INVENTOR(S) : Robert N. Blumenthal and Andreas T. Melville It is certified that error appears in the above-identified patent and that said Letters Patent are hereby corrected as shown below:

Claim 5, column 7, line 15 - before "surface" insert

--other--

Claim 7, column 7, line 43 - after "surface" change "againt"

to --against--

Claim 8, column 8, line 3 - change "characteristics" to

--characteristic--

Signed and Sealed this

Fifteenth Day of May 1979

[SEAL]

Attest:

RUTH C. MASON
Attesting Officer

DONALD W. BANNER
Commissioner of Patents and Trademarks